(12) United States Patent
Issadore et al.

(10) Patent No.: US 10,473,590 B2
(45) Date of Patent: Nov. 12, 2019

(54) APPARATUS AND METHODS FOR ANALYZING THE OUTPUT OF MICROFLUIDIC DEVICES

(71) Applicant: The Trustees of the University of Pennsylvania, Philadelphia, PA (US)

(72) Inventors: David Issadore, Philadelphia, PA (US); Melaku Muluneh Woldemariam, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 147 days.

(21) Appl. No.: 15/503,592

(22) PCT Filed: Aug. 14, 2015

(86) PCT No.: PCT/US2015/045235
§ 371 (c)(1),
(2) Date: Feb. 13, 2017

(87) PCT Pub. No.: WO2016/025809
PCT Pub. Date: Feb. 18, 2016

(65) Prior Publication Data
US 2017/0234795 A1 Aug. 17, 2017

Related U.S. Application Data

(60) Provisional application No. 62/037,273, filed on Aug. 14, 2014.

(51) Int. Cl.
*G01N 21/64* (2006.01)
*B01L 3/00* (2006.01)
*G01N 21/25* (2006.01)

(52) U.S. Cl.
CPC .... *G01N 21/6428* (2013.01); *B01L 3/502784* (2013.01); *B01L 3/502715* (2013.01);
(Continued)

(58) Field of Classification Search
CPC ..... B01L 2300/0627; B01L 2300/0861; B01L 3/502784; G01N 21/6428; G01N 2201/063
See application file for complete search history.

(56) References Cited

U.S. PATENT DOCUMENTS 7,701,580 B2 4/2010 Bassler
8,476,382 B2 * 7/2013 Kumacheva .......... B01F 3/0807
137/806
(Continued)

FOREIGN PATENT DOCUMENTS

JP 2005-538727 A 12/2005
JP 2008-185585 A 8/2008
(Continued)

OTHER PUBLICATIONS

MacWilliams et al., "Pseudo-Randon Sequences and Arrays", Proceedings of the IEEE, vol. 64, 1976, pp. 1715-1729.
(Continued)

*Primary Examiner* — Jennifer Wecker
(74) *Attorney, Agent, or Firm* — BakerHostetler (57) ABSTRACT

Microfluidic devices for analyzing droplets are disclosed. A described microfluidic device includes a substrate and a microfluidic channel formed on the substrate. The microfluidic channel includes passages where each passage has a mask pattern configured to modulate a signal of a droplet passing through that passage, such that droplets passing through the passages produce signals. The microfluidic device also includes a detector configured to detect the signals. Methods of analyzing droplets with a microfluidic device having a microfluidic channel formed on a substrate are disclosed. A described method includes passing droplets
(Continued)

through the passages, modulating signals from the droplets using mask patterns, formed on the passages; and detecting the signals.

29 Claims, 9 Drawing Sheets

(52) U.S. Cl.
 CPC .......... *B01L 2300/0627* (2013.01); *B01L 2300/0861* (2013.01); *G01N 2201/063* (2013.01)

(56) References Cited

U.S. PATENT DOCUMENTS

| | | | |
|---|---|---|---|
| 9,029,800 B2 | 5/2015 | Kiesel et al. | |
| 2003/0234210 A1 | 12/2003 | Deshpande et al. | |
| 2011/0222062 A1* | 9/2011 | Martini | G01N 21/05 356/417 |
| 2013/0016335 A1 | 1/2013 | Lo | |
| 2013/0037726 A1* | 2/2013 | Kiesel | G01J 3/36 250/458.1 |

FOREIGN PATENT DOCUMENTS

| | | |
|---|---|---|
| JP | 2009-180723 A | 8/2009 |
| WO | 2010104993 A2 | 9/2010 |
| WO | 2011008233 A1 | 1/2011 |

OTHER PUBLICATIONS

International Search Report and Written Opinion of the International Searching Authority for International Application No. PCT/US2015/045235, dated Nov. 13, 2015, 8 pages.
Martini, J., et al., "Time encoded multicolor fluorescence detection in a microfluidic flow cytometer," Lab on a Chip, vol. 12, No. 23, Aug. 29, 2012, pp. 5057-5062.
Piyasena, M.E., et al., "The intersection of flow cytometry with microfluidics and microfabrication," Lab on a Chip, vol. 14, No. 6, Jan. 14, 2014, pp. 1044-1059.
Kiesel, P., et al., "Monitoring CD4 in whole blood with an optofluidic detector based on spatially modulated fluorescence emission," Cytometry, Part A, vol. 79A, No. 4, Apr. 22, 2011, pp. 317-324.
Boyle, D.S., et al., "Emerging technologies for point-of-care CD4 T-lymphocyte counting," Trends in Biotechnology, Jan. 2012, pp. 45-54.
Extended European Search Report for European Application No. 15 831 303.1, dated Feb. 14, 2018, 12 pages.
International Preliminary Report on Patentability and Written Opinion for International Application No. PCT/US2015/045235, dated Feb. 14, 2017, 7 pages.

* cited by examiner

APPARATUS AND METHODS FOR ANALYZING THE OUTPUT OF MICROFLUIDIC DEVICES

CROSS REFERENCE TO RELATED APPLICATIONS

This application is a national phase application of International Application No. PCT/US2015/045235, filed Aug. 14, 2015 entitled APPARATUS AND METHODS FOR ANALYZING THE OUTPUT OF MICROFLUIDIC DEVICES which claims priority to U.S. Provisional Patent Application No. 62/037,273, filed Aug. 14, 2014, the disclosure of which is incorporated herein by reference in its entirety for all purposes.

FIELD OF THE INVENTION

This invention relates to the field of microfluidics and, more particularly, devices and processes for analyzing the output of microfluidic devices such as droplets.

BACKGROUND OF THE INVENTION

Droplet-based assays, in which micro-scale emulsions are used as isolated compartments to run many independent chemical reactions, have gained popularity in recent years as a platform for a wide range of biomedical applications. Compared to the conventional laboratory approach of using millimeter-sized well plates to isolate fluids, micrometer-scale droplets contain only picoliters (10-12 L) of fluid, offering a $10^6 \times$ reduction in volume. Furthermore, compared to the hundreds of compartments available on a conventional well plate, microfluidics allow droplets to be created at rates as high as $10^6$ per minute, offering a greater than $10^4$ times increase in the number of compartments over conventional techniques. The enormous increase in sensitivity that comes from massively parallelized, ultra-small volume assays, has been harnessed to detect both single molecules of protein and nucleic acid, to monitor molecular concentrations as a function of time, to perform high-throughput screens for directed evolution, and to assay single cells.

While the microfluidics to produce and process droplets can be miniaturized and integrated onto compact, monolithic chips, the read-out of droplet-based assays have been more difficult to miniaturize. Fluorescence-based sensing may be used because: 1) molecular beacons, which can turn on or off fluorescence based on binding events, obviate extra steps to wash away excess reagents; 2) differently colored fluorophores allow for the detection of multiple targets in a single droplet; and 3) widely available fluorescence-based reagents ease assay development. Previous work has been done to integrate fluorescence detection with droplet microfluidics and to miniaturize fluorescence detection of cells. Wide-field microscopy techniques have been developed that can take micrographs of static droplets, with an ability to resolve as many as $10^6$ in a single-shot. Other groups have developed in-flow detection systems, which have the advantage of real-time sorting, down-stream processing, and an ability to measure a far greater number of droplets than possible with the static techniques, measuring as many as $10^4$ droplets per second. However, these techniques require complex optics and are not easily amenable to monitoring more than one channel.

SUMMARY OF THE INVENTION

Aspects of the invention relate to devices and processes for analyzing the output of microfluidic devices.

In accordance with one aspect, the invention provides a microfluidic device for analyzing droplets. The microfluidic device includes a substrate and a microfluidic channel formed on the substrate. The microfluidic channel includes a plurality of passages, each of the plurality of passages having a mask pattern configured to modulate a signal of a droplet passing through that passage, such that droplets passing through the plurality of passages produce a plurality of signals. The microfluidic device also includes a detector configured to detect the plurality of signals.

In accordance with another aspect, the invention provides a microfluidic device for analyzing droplets. The microfluidic device includes a substrate and a microfluidic channel formed on the substrate. The microfluidic channel includes a plurality of passages, each of the plurality of passages having a mask pattern. Each mask pattern is configured to modulate a fluorescence signal of a droplet passing through the passage, such that droplets passing through the plurality of passages produce a plurality of fluorescence signals. The microfluidic device also includes a detector configured to simultaneously detect the plurality of fluorescence signals.

In accordance with yet another aspect, the invention provides a method of analyzing a plurality of droplets with a microfluidic device having a microfluidic channel formed on a substrate, the microfluidic channel including a plurality of passages. The method includes the steps of passing a plurality of droplets through the plurality of passages; using a plurality of mask patterns formed on the plurality of passages, modulating a plurality of signals from the plurality of droplets; and detecting the plurality of signals.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

Aspects of the invention are directed to devices and processes for analyzing the output of microfluidic devices.

The inventors have recognized that it would be useful to provide for the bulk analysis of the output of a microfluidic device. The inventors have also recognized that encoding of the signal from the output, e.g., droplets, using distinct micro-patterned masks for each channel of the microfluidic device enables the recovery of weak signals without the need for expensive and bulky optical detectors. The inventors have further recognized that the use of masks permits multiple channels to be simultaneously monitored, allowing increasingly complex experiments without the need for additional and expensive detection hardware such as, e.g., lenses, lasers, and complex fluid control hardware. In particular, the inventive microfluidic device can measure droplets in multiple channels using a single detector, even simultaneously, and does not require lenses or sophisticated fluid flow control. Thus, embodiments of the microfluidic devices are suitable for portable, point-of-care use.

As used herein, "droplet" refers generally to a vehicle and/or delivery system for one or more analytes to be analyzed using the devices and processes of the present invention. Within the context of microfluidic devices, suitable analytes include, but are not limited to, emulsions (e.g., water-in-oil, oil-in-water, water-in-oil-in-water), vesicles, microbubbles, beads (e.g. magnetic polymer beads), cells, pathogens, DNA, RNA, nucleic acids, pollutants, and the like.

As used herein, "signal" refers to any externally detectable characteristic of the droplet. Exemplary signals which may be detected by the inventive microfluidic device include electronic, magnetic, dielectric, ultrasound, fluorescence signals.

Figure 1A:
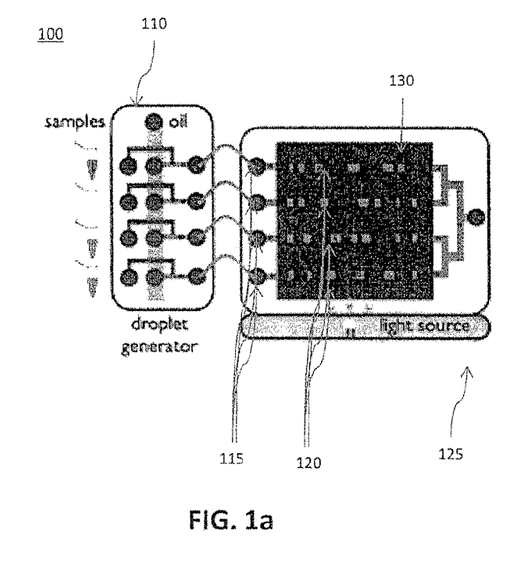
FIG. 1a is a schematic illustration of a microfluidic device according to aspects of the present invention.

FIG. 1a shows a schematic illustration of a microfluidic device 100 for analyzing droplets according to aspects of the present invention. The inventive microfluidic device permits the analysis of droplets, such as monodisperse emulsions which may be generated by a droplet generator 110. In one embodiment, droplet generator 110 is a component of microfluidic device 100.

Portions of microfluidic device 100 may be formed on a substrate. Exemplary substrate materials include glass, silica, mylar, polysiloxanes, or carbon-based polymers including, but not limited to polydimethylsiloxane ("PDMS"), a polyacrylamide, a polyacrylate, a polymethacrylate or a mixtures thereof.

Microfluidic device 100 includes a plurality of passages through which droplets may flow which, collectively, may be referred to as a microfluidic channel. The microfluidic channel includes a plurality of fluid passages 115. Plurality of fluid passages 115 are in fluid communication with, and receive droplets from, droplet generator 110. In an exemplary embodiment, each of the plurality of fluid passages 115 includes a stream of droplets which originate in droplet generator 110.

Figure 1B:
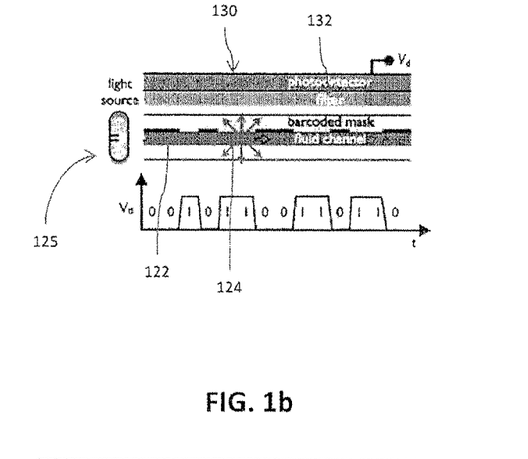
FIG. 1b is a cross-sectional schematic illustration of a microfluidic device according to aspects of the present invention.

Each of the plurality of passages 115 includes a respective mask pattern (collectively mask 120), which is configured to modulate a signal produced by the droplet passing through the passage. Although illustrated as a single mask 120, one of skill in the art will recognize from the description herein that each mask pattern may be implemented as an independent mask or two or more mask patterns may be combined into one mask. In one embodiment, mask 120 is a micropattern (e.g., "barcode"), which resides on one or more surfaces of each passage in the plurality of passages. Turning to FIG. 1b, each mask pattern is comprised of one or more signal emitting portions and one or more signal dampening portions. For example, where the signal to be analyzed is fluorescence, the signal emitting portions may be transparent portions 124 which permit the signal (here, light) to pass through the mask and the signal dampening portions may be opaque portions 122 that prevent transmission of the signal through the mask. The signal emitting portions and the signal dampening portions may include various states of transparency between fully transparent and fully opaque. Here, the mask may be lithographically patterned metal on glass that may also serve as the roof of the plurality of passages 115. One of ordinary skill in the art will understand that mask 120 may be formed on other surfaces (i.e., the side or base of the plurality of passages 115). Mask 120 may also be formed on an internal surface of the plurality of passages 115, or on a surface above the plurality of passages (such as, e.g., an optical filter above the plurality of passages).

Where other signals are of interest, such as one or more of electronic, magnetic, dielectric, and ultrasound signals, mask 120 may be comprised of other than varying states of transparency. That is, the signal emitting portion should permit all or a portion of the signal of interest to pass through the mask, while the signal dampening portion should prevent such transmission. For example, with respect to magnetic signals, mask 120 could include magnetic field sensors positioned on the passages at varying positions to encode the mask pattern. Alternatively, a high susceptibility material such as NiFe that would act to shield a sensor from the magnetic field could be patterned onto the plurality of passages 115 to achieve the same result. Where the signal of interest is ultrasound, the mask pattern may be generated using a material having a large reflection coefficient.

Turning back to FIG. 1*a*, where fluorescence is the signal to be analyzed, microfluidic device 100 may also include an illuminator, e.g., light source 125. Light source 125, as depicted, is a side-illumination system which acts to excite the fluorescent dyes within the droplets. Light source 125 may be a light emitting diode (LED) which emits light tuned to the excitation wavelength of the fluorophore $\lambda_{ex}$ within the droplets. Light source 125 may be configured to emit light at two or more light wavelengths tuned to the excitation wavelengths of two or more fluorophores. Alternatively, two or more light sources may be utilized to emit light having two or more two or more light wavelengths. The illuminator may be configured to modulate the emitted two or more light wavelengths out of phase from one another.

Light source 125 may be configured to alternate between illuminating and not illuminating and/or alternate between two or more light wavelengths. Desirably, the alternating occurs numerous times per each droplet's duration under an individual pixel, e.g., per the duration under a single pixel, a droplet may undergo 100 alternations, 200 alternations, 300 alternations, etc. In one embodiment, the alternating between the two or more light wavelengths occurs at a frequency of 300 kHz, such that each droplet undergoes 300 alternations of excitation as each droplet passes under a single, individual pixel. Employing an illuminator configured to alternate between illuminating and not illuminating and/or alternate between two or more light wavelengths may enable microfluidic device 100 to measure the relative fluorescence signal, as opposed to the absolute signal, for each droplet, thereby facilitating improved, calibration free analysis of the analytes.

Anti-resonant coupling may be used to contain the light within the microchip and uniformly and intensely illuminates the fluid channel. A droplet containing one or more fluorescent dyes, passing through plurality of passages 115, will absorb the excitation light from light source 125 and fluoresce. As the droplet moves down passage 115, its emitted light is amplitude modulated by mask 120.

Microfluidic device 100 also includes a detector 130, which detects the modulated signal emitted from each of the plurality of passages 115. Detector 130 may be configured to simultaneously detect the modulated signals emitting from each of the plurality of passages 115. In one embodiment, as depicted in FIG. 1*b*, isotropically emitted fluorescence light from a passage passes through a respective mask pattern of mask 120 and into a detector 130, e.g., a silicon photodetector. In the illustrated embodiment, between mask 120 and detector 130, is a long pass optical filter 132, which diminishes background signal from scattered excitation light. In one embodiment, where light source 125 produces light at two or more light wavelengths, an additional optical filter may be employed such that two or more optical filters are utilized, each corresponding to a single wavelength of the two or more light wavelengths, and positioned between the mask pattern and the photodetector. The two or more filters may be configured to demodulate the two or more fluorescent signals. The two or more filters may also be configured as long-pass filters and spatially separated such that each droplet passes under each filter sequentially. Detector 130 may sit directly on top of mask 120.

As the droplet passes under a mask pattern, its emitted light transitions from being blocked by signal dampening portion 122 to being transmitted by signal emitting portion 124, which results in a binary, amplitude modulated signal $V_d(t)$. In one embodiment, the mask pattern $m_n$, for each of the n plurality of passages 115, may be defined as a series of 1s and 0s, with 1 corresponding to transparent and 0 corresponding to opaque. Positioning mask 120 in close proximity to the droplets ensures that each bit in the mask pattern subtends the largest possible solid angle of light emitted from the droplets and, therefore, ensures contrast between 1s and 0s.

Mask patterns may range from 80 to 125 bits. In one embodiment, the mask pattern is greater than 100 bits. In one system (SNR=−6 dB, c=4 channels) it was found that the mask length could be reduced to as low as L=100 bits, (AUC=0.999) without a significant reduction in performance. Below L=50 bits in such a system, sensitivity and specificity may degenerate appreciably.

Mask patterns within mask 120 may desirably minimally correlate with each other, such that the energy $E(m_a*m_a)$ is minimal. This permits the droplets to be concurrently present in the detection region in a different passage of the same channel and be distinguished from one another. Preferably, the mask pattern is different for each of the plurality of passages 115. In one embodiment, mask patterns may minimally cross-correlate with one another, such that the energy $E(m_a*m_b)$ is minimal for a≠b. This permits the signals from different channels to be maximally separable.

Pseudorandom vectors, known as maximum length sequences (MLS), can be generated using a feedback register. For a sequence of length $L=2^M-1$, the shift register's elements are defined by a primitive polynomial h(x) of degree M. By iterating this shift register, a series of 1s and 0s can be generated that can be proven to be minimally autocorrelated. To create multiple channels, a two-dimensional MLS may be generated by folding the one-dimensional MLS into a two-dimensional array as described by MacWilliams and Sloane, Pseudo-random sequences and arrays. *Proceedings of the IEEE* 64:1715-1729 (1976).

Figure 1C:
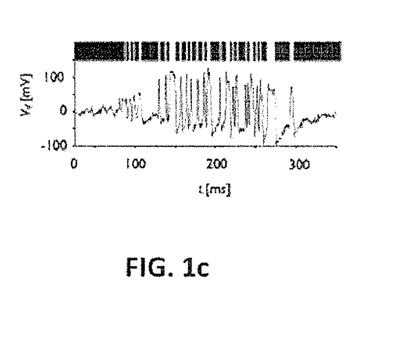
FIG. 1c is a graph depicting the amplitude modulated signal resulting from a 105 bit long mask pattern according to aspects of the present invention.

The mask patterning allows the one-dimensional signal obtained by detector 130 to be decompressed into a set of vectors, each representing one of the plurality of passages 115. FIG. 1*c* graphically illustrates an example of a 105 bit long mask pattern, and the corresponding amplitude modulated signal $V_d$ from a passing droplet. This time encoding serves two functions: 1) it allows the recovery of weak signals (SNR<<1) using correlation-based signal recovery, and therefore enables a simple hardware implementation that does not include lenses, lasers, or highly sensitive detectors; and 2) it allows for independent monitoring of multiple channels using only a single detector, enabling additional assays to be implemented on a single chip without having to add to the complexity of the hardware.

The length of each bit may be uniform. In one embodiment, the bit length is 80 μm long, resulting in an 8.4 mm long detection region for a 105 bit long mask pattern. One of ordinary skill in the art will understand that bit length may also vary from bit to bit.

Figure 1D:
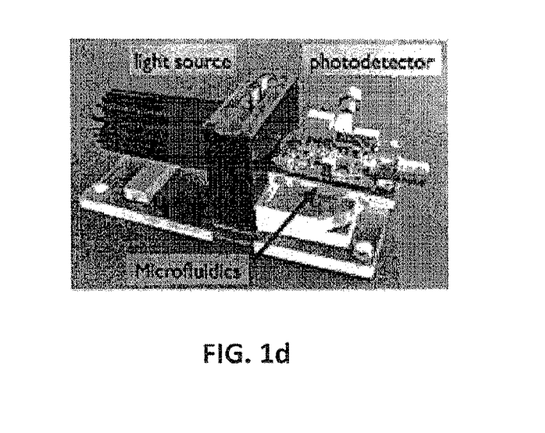
FIG. 1d is a photograph of a microfluidic device according to aspects of the present invention.

FIG. 1d is a photograph of microfluidic device 100 for analyzing droplets according to aspects of the present invention. In this embodiment, the system is roughly the size of a cell phone (10×5×2 cm³).

Figure 2A:
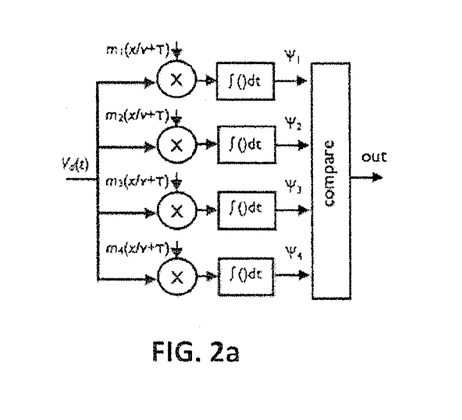
FIG. 2a is a flow diagram schematic of signal measurement according to aspects of the present invention.

Processing the signal from the photodetector $V_d(t)$ may include the preliminary determination of whether a fluorescent droplet has passed through the detection region, and if so, to determine which of the plurality of passages 115 it passed through. To this end, microfluidic device 100 may also include a circuit configured to correlate each of the plurality of fluorescence signals with a mask pattern. The signal may be projected onto a set of vectors ψn, each representing the relative correlation of the signal from the passing droplet Vd(t) and each of the masks $m_n$. As depicted in FIG. 2a, the signal measured by the photodetector Vd(t) is projected into vectors $\psi n(\tau) = Vd(t) * m_n(x/v) = \int Vd(t) m_n(x/v+\tau)dt$ from $-\infty$ to $\infty$, each representing the likelihood of the droplet having passed through an individual channel n and traveling at velocity v.

Figure 2B:
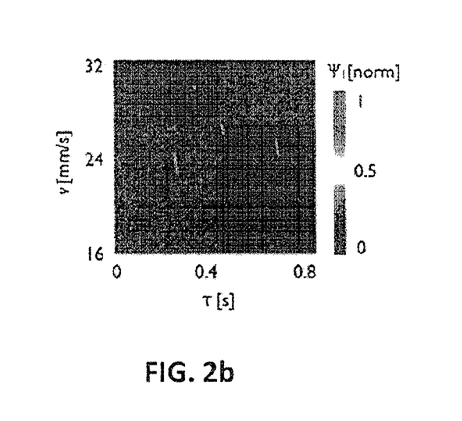
FIG. 2b is a two dimensional velocity correlation according to aspects of the present invention.
Figure 2C:
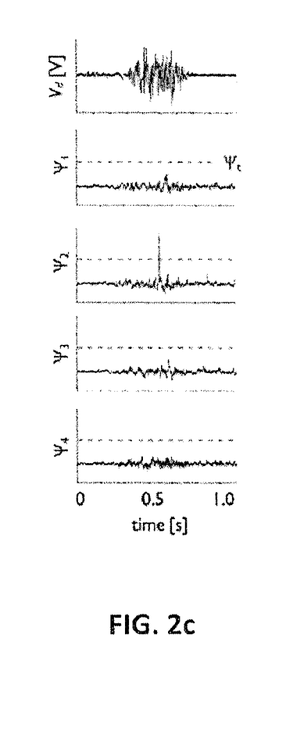
FIG. 2c is a set of graphs relating to raw signal data and the corresponding orthogonal correlation vectors according to aspects of the present invention.

An example of raw data that comes from the photodetector as a droplet, loaded with 10 nM rhodamine, passes through the detection region is shown as $V_d$ in FIG. 2c. After the signal is passed through the bank of correlators (FIG. 2a), a set of vectors are generated, ψ4, ψ2, ψ3, and ψ4, with each vector corresponding to a particular channel in plurality of passages 115. The droplet causes a large peak in ψ2, suggesting that the droplet passed through that channel. We define a gating threshold value ψt that is applied to each of these vectors (shown as a green dashed line) above which we consider a fluorescent droplet detected.

The peak detection described above may be enhanced with knowledge of the droplet's velocity. The inventors have found that droplet and flow control is, however, not necessary. In particular, an algorithm adaptable to droplets with dispersed velocities may be used. A two-dimensional correlation $m_n, (x/V)*Vd(t)$ may be calculated, where V is a 1-d matrix with a range of velocities [vmin:vmax]. This two-dimensional correlation may be calculated using MATLAB. FIG. 2b depicts the output as a two-dimensional matrix in velocity v and time t, from which peak positions (vp,tp) could accurately be found in the 2-d space. An assumption of this technique is that the droplet velocity is constant for the duration of time (~50 ms) in the detection region, which we verified experimentally. In this particular embodiment, three droplets at three distinct velocities may be observed.

Detection may be further improved by alternating light source 125 between illuminating and not illuminating and/or alternating between two or more light wavelengths. By modulating the excitation light, the signal may be shifted in frequency away from the low frequency noise of the photodetector 130, thereby improving the capability to detect low SNR droplets. By encoding the response of the droplet from the two excitation sources and two emission filters, each droplet is independently measured with the four possible combinations. In one embodiment, three parameters may be measured to detect the presence of droplets, e.g., two fluorescence channels and brightfield scattering (SSC).

Figure 5:
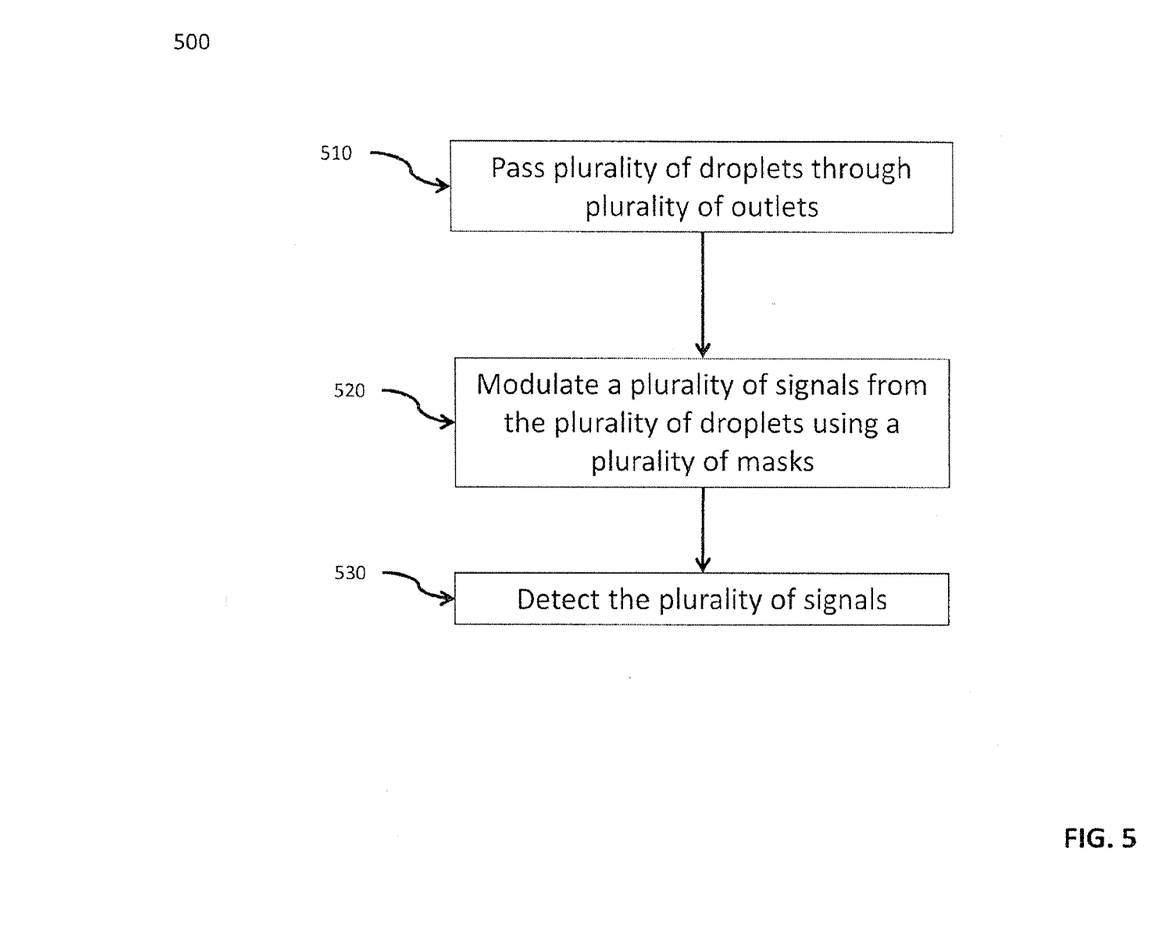
FIG. 5 is a flow diagram depicting selected steps of a method of analyzing a plurality of droplets according to aspects of the present invention.

Turning to FIG. 5, a flow diagram depicting selected steps of a process of analyzing a plurality of droplets with a microfluidic device having a microfluidic channel formed on a substrate, the microfluidic channel including a plurality of passages is provided. It should be noted that, with respect to the methods described herein, it will be understood from the description herein that one or more steps may be omitted and/or performed out of the described sequence of the method (including simultaneously) while still achieving the desired result.

In step 510, a plurality of droplets are passed through a plurality of passages (e.g. plurality of passages 115; FIG. 1a). The plurality of droplets may be generated by, e.g., droplet generator 110.

In step 520, a plurality of signals from the plurality of droplets are modulated using a plurality of mask patterns formed on the plurality of passages (e.g., mask 120; FIG. 1a). Each mask pattern may have one or more signal emitting portions and one or more signal dampening portions. Where the signal to be detected is fluorescence or light, the one or more signal emitting portions may be transparent portions and the one or more signal dampening portions may be opaque portions. Further, the one or more signal emitting portions may form a pattern of various states of transparency. The transparent portions and the opaque portions of the plurality of masks may, preferably, correspond to a binary pattern having at least about 100 bits. In one embodiment, each of the plurality of passages has a corresponding mask from the plurality of masks.

In step 530, the plurality of signals are detected. The plurality of signals may be detected using a detector 130, e.g., a photodetector. The detector may be positioned directly against mask 120, or a filter 132 may be positioned between the detector (e.g. photodetector 130) and the mask 120.

In an embodiment, where the signal is a fluorescence signal and the detector is a photodetector, the plurality of passages are illuminated prior to step 530. Alternating the illumination of the plurality of passages, e.g., by way of alternating the illuminator between illuminating and not illuminating and/or alternating between two or more light wavelengths, may facilitate detection of the fluorescence signal(s). In one embodiment, alternating the illumination of the plurality of passages comprises repeatedly turning an illuminator, e.g., light source 125, on and off. In another embodiment, alternating the illumination of the plurality of passages comprises alternating between two or more lights, each having one or more light wavelengths. Each light may be configured to have one or more light wavelengths that are different from the one or more light wavelengths comprising the other lights. For example, the step of illuminating the plurality of passages may comprise an illuminator, the illuminator being configured to produce two or more lights, each light having a light wavelength, and alternating between the two or more lights during the step of illuminating the plurality of passages.

The droplets may include two or more fluorescent dyes to produce two or more pluralities of fluorescent signals. Each plurality of fluorescent signal may correspond to a different light wavelength and/or may have a different emission spectra.

The plurality of signals detected by the detector may additionally be correlated to a corresponding mask of the plurality of masks.

EXAMPLES

The following examples are included to demonstrate the overall nature of the present invention. The examples further illustrate the improved results obtained by generating stable monodisperse microbubbles and by employing the microfluidic device and related processes according to principles of the present invention.

Figure 3A:
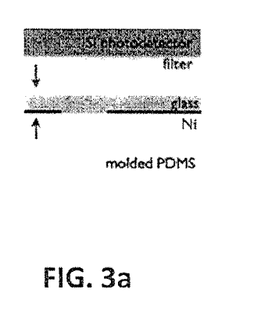
FIG. 3a is a cross-sectional schematic illustration of a microfluidic device according to aspects of the present invention.
Figure 3B:
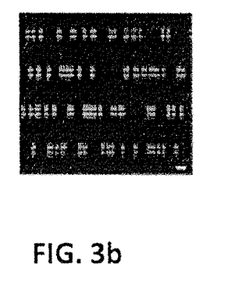
FIG. 3b is an optical micrograph of a portion of the device according to aspects of the present invention.

As shown by FIG. 3a, the device was fabricated using a combination of soft lithography to make molded PDMS fluidic channels and standard planar lithography of Ni on glass to create the masks. The Si photodetector sits immediately on top of the chip, a filter is used to block scattered excitation light. The molded PDMS layer was fabricated using standard single-layer SU-8 lithography (SU-8 2025, MicroChem) with 80 µm thick features. The mask was patterned into Ni on glass, using standard planar photolithography. First, Ni was thermal evaporated onto glass slides (Kurt Lesker PVD 75, Wolf Nanofabrication Facility, University of Pennsylvania). Subsequently, the mask pattern was lithographically defined (Shipley 1813) using wet etching of the Ni (Iron (III) Chloride). The Ni patterned glass slide was permanently bonded to the molded PDMS layer using PDMS-stamped bonding. FIG. 3b depicts an optical micrograph of a portion of the device. The scale bar is 160 µm.

Figure 3C:
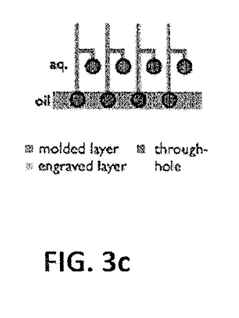
FIG. 3c is a schematic of a microfluidic device according to aspects of the present invention.
Figure 3D:
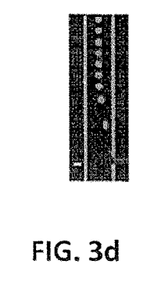
FIG. 3d is fluorescence micrograph according to aspects of the present invention.

As depicted by FIG. 3c, droplets were generated using T-Junctions. The droplets were loaded with rhodamine. The scale bar is 60 µm. Four T-Junctions were integrated onto a single device, with only a single oil input, using hybrid soft-lithography/laser machining. The chip was fabricated using a combination of 1) soft lithography to make microscale droplet makers and fluidic channels in a layer of PDMS, and 2) direct laser micromachining to make vias to a second layer of PDMS that has a deeper (d=200 µm) laser-engraved channels to deliver oil evenly to the individual droplet makers. The T junction's aperture was 100 µm wide and 50 µm deep. Mineral oil was used as the continuous phase, with 5% V/V Span 80 and 1% V/V Tween (Fisher Scientific). Flow rates were 0.1 mL/hr for the aqueous phase and 1 mL/hr for the oil phase, and were controlled using syringe pumps (Braintree Scientific). As shown by FIG. 3d, the mean droplet size was 60 µm and the CV was ~5%. Using on-chip reservoirs for the four aqueous inputs, and connecting the two chips together using tygon tubing, a single syringe pump was capable of driving the device. Using tubing to connect two separate chip modules was done for convenient prototyping. The droplet generator and detection module, made using compatible fabrication strategies, were also integrated onto the same chip.

Figure 3E:
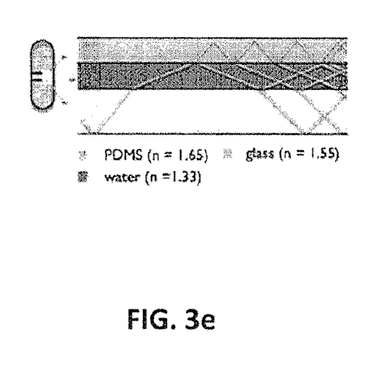
FIG. 3e is a schematic of a microfluidic device according to aspects of the present invention.
Figure 3F:
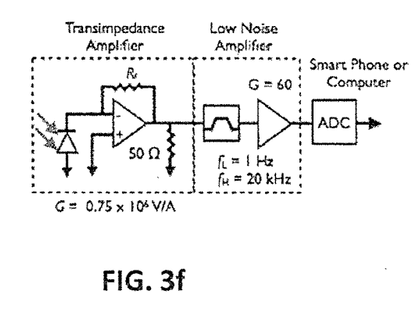
FIG. 3f is a chip schematic of a signal detector according to aspects of the present invention.

As depicted by FIG. 3f, the output current from the photodetector was amplified, digitized, and processed using custom electronics. The photodetector sensor had a responsivity of 200 mA/W at $\lambda$=600 nm. The photodetector was connected to a G=0.75×106 V/A transimpedance amplifier with a DC-20 kHz bandwidth (Thor PD100A). The output of the transimpedance amplifier was AC coupled to a preamplifier (PA) with a gain of 20, and a high-pass frequency of fH=1 Hz and a low pass frequency of 20 kHz (Ithaco). The output of the PA was connected to an analog to digital converter (National Instruments, NI USB-6009), which digitized the signal at 40 kS/s before sending the signal to a computer or smart phone over USB for analysis, All analysis was done on a personal computer (MATLAB), but for a portable implementation this processing could be done using either a digital signal processing (DSP) chip or using cloud computing.

FIG. 3e depicts a schematic showing how antiresonant coupling was used to deliver light via side illumination into the chip.

The optics in the chip were kept as small and inexpensive as possible, using commercial products that could be packaged into a small-footprint, portable device (FIG. 1d). The excitation light was provided by an ultra-bright LED ($\lambda$ex=530 nm) (Luminus, CBT-90-G-C11-3K201) packaged into a custom laser machined (Universal Laser) acrylic box with heat sink (Wakefield Thermal Solutions, 19757-M-AB). The box was design such that the chip could slide into it, similar to a slot connector, and the light would couple to the chip at an oblique angle for maximum anti-resonant coupling. A silicon photodetector mounted on a printed circuit board, with integrated transimpedance amplification was used (Thor Labs, PDA 100a). A $\lambda$=600 nm long pass filter (#69-868 Edmund optics) was placed between the chip and detector to diminish (95% reflectance) the effect of scattered light at the excitation wavelength.

The length of the mask patterns for the device was 105 bits. The sequence was made as long as possible to minimize each channel's autocorrelation and the cross-correlation between channels. Its length was constrained by the size of the photodetector. The Silicon photodetector (Thor Labs, PDA100A) was 10×10 mm$^2$, and since no lenses were used, this set the size of the detection region. The size of each pixel in the mask was determined by the size of the droplets. To ensure that a large fraction of the isotropically emitted light from each droplet was blocked by the mask pattern, the pixel size of the mask was matched to that of the droplets. 60 µm droplets and 80 µm pixels were used. The total number of bits per channel was, thus, constrained to be 10 mm/80 µm=125.

To create a set of masks each 105 bits long, which matched our specifications for minimal auto and cross-correlation, the process in MacWilliams and Sloane was employed to create a pseudo random matrix array from pseudo random maximum length sequences (MLS), The dimensions of the pseudo random matrix are certain permissible factorizations of the MLS sequence. In this case, the dimensions were 105×39=4095=2$^{12}$−1 (M=12). These sequences were compared to randomly generated sequences of masks using MATLAB. It was found that the MLS generated masks have a significantly smaller autocorrelation and cross-correlation (P<10$^{-4}$, two-tailed t test). An alternative strategy to generate masks was also developed, in which a large library of random masks were generated, and then a subset of masks that had low autocorrelation were selected. From that subset, a subset of pairs that had low cross-correlation were then selected, and from those pairs, sets of four that have low cross-correlation. The two procedures yielded similar results, but the MLS technique took only a few seconds of computation time whereas the selection technique took several hours, and became untenably slow for greater than four channels. Both implementations were performed in MATLAB.

Measuring Fluorescent Droplets Below the Noise Floor

Figure 4A:
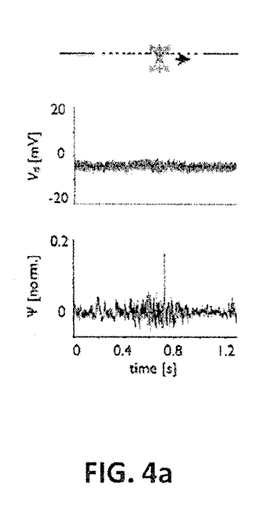
FIG. 4a is a set of graphs relating to raw signal data and the corresponding orthogonal correlation vectors according to aspects of the present invention.

The inventors' correlation-based detection scheme allows extremely weak signals (SNR<<1) to be recovered from below the noise floor. This platform can efficiently separate signal from the noise because the signal correlates with the pattern of the mask, whereas the noise does not. The capability to recover weak signals is desirable because it allows for lens-free use, making it well suited for miniaturization. To demonstrate this capability, weakly fluorescent droplets were measured with an SNR~0.25, which could not be resolved in the raw data. As shown in FIG. 4a, the signal to noise ratio is calculated by dividing the expected energy in the signal from a passing droplet by the average energy of the noise over the same time interval. However, after correlating this data with the correct mask $m_2$, the peak in its correlation vector $\psi$ was well above the noise floor (SNR>10) in the correlation data and easily detected.

Measuring Multiple Droplets in the Detection Region Simultaneously

The high sensitivity of the inventive platform comes partially from the detection region's large area (10×10 $mm^2$), which collects many photons from fluorescing droplets as they pass. However, the trade-off for having a large detection region is that, the detection region is limited to one droplet at a time as in conventional cytometry, it severely limits the device's throughput. To this end, the masks were designed to be capable of resolving multiple droplets within the detection region simultaneously. Mask patterns were chosen that have low autocorrelation and low cross-correlation with one another, such that our cross-correlation-based detection strategy could resolve droplets in different positions along the same channel or in different channels concurrently.

Figure 4B:
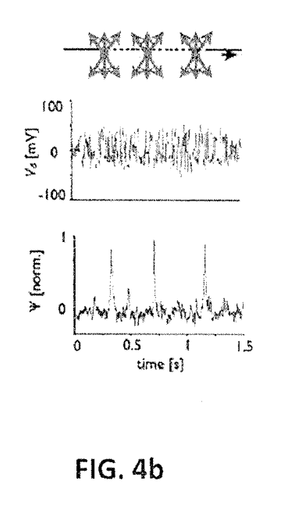
FIG. 4b is a set of graphs relating to raw signal data for multiple droplets and the corresponding orthogonal correlation vectors according to aspects of the present invention.

To demonstrate this capability, three droplets which passed through the detection region were measured concurrently, all in the same channel. As shown in FIG. 4b, in the raw data, the three signals overlap and are not possible to resolve. However, after correlating this data with the correct mask, the three peaks in the correlation vector $\psi$ become well separated and could be individually resolved.

Multichannel Detection

Figure 6A:
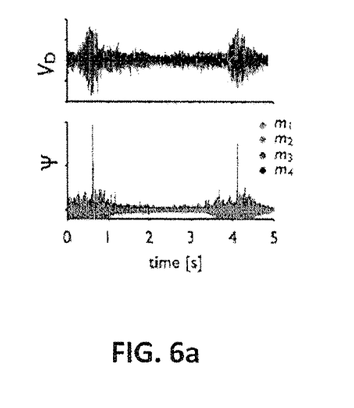
FIG. 6a is a set of graphs depicting the passage of two droplets through mask patterned passages according to aspects of the present invention.

A benefit of the inventive platform is the ability to detect droplets in multiple channels simultaneously. To characterize this capability, droplets were sent through specific channels and the output of the device was compared to the expected outcomes. This functionality is demonstrated in FIG. 6a, which shows two droplets passing through the detection region, one of the droplets passing in channel 1 and the other in channel 2. After correlating this data with the correct masks, a clear peak in channel 2 corresponds to the first droplet and a clear peak in channel 1 corresponds to the second droplet, allowing the droplet's correct channel to be readily identified.

Quantification of Device Sensitivity and Specificity

To characterize the tradeoff between sensitivity and specificity, the inventive device was tested using a range of threshold values $\psi_t$ and generated a receiver operator characteristic curve (ROC). Sensitivity=TP/P, where TP is the number of instances the detector successfully detected a passing droplet and correctly identified its channel and P is the total number of droplets. Specificity=TN/N of the detector, where TN=N−FP is the true negatives and is defined by the total false positives FP, the instances when the detector falsely detects a droplet and the total number of negatives N=P*(c−1), which is defined by P the total number of droplets and c the total number of channels.

Figure 6B:
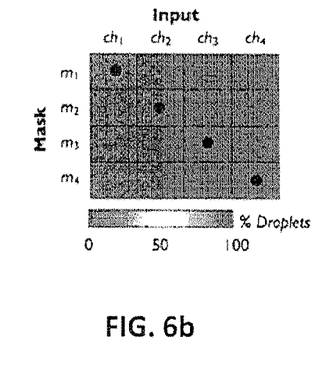
FIG. 6b is a heat map depicting the passage of droplets through mask patterned passages according to aspects of the present invention.

Droplets were first passed through one of the four channels at a time and quantified the sensitivity and specificity of detection. FIG. 6b summarizes results of the experiments in a heat map. The device performed as expected; droplets were detected in the channels where droplets were passing, along the diagonal of the heat map, and not in the incorrect channels, off diagonal. Black dots show the channels where droplets were passed. For each of the tests, we passed ~400 droplets with an SNR~1. For the threshold value $\psi_t$ chosen, the sensitivity was 1.0 and the specificity was 0.994.

Figure 6C:
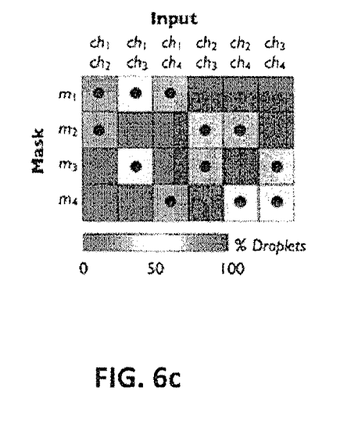
FIG. 6c is a heat map depicting the passage of droplets through mask patterned passages according to aspects of the present invention.

To demonstrate the chip's ability to simultaneously detect droplets in multiple channels, droplets were next passed through each of the six possible sets of channels (ch1 & ch2, ch1 & ch3, etc.). FIG. 6c summarizes the results of the experiments in a heat map. Droplets were detected in the correct sets of channels and not in the incorrect channels. For each of the tests, ~800 droplets were passed with an SNR~1. For the threshold value $\psi_t$ chosen, the average sensitivity was 1.0 and the specificity was 0.993.

Figure 6D:
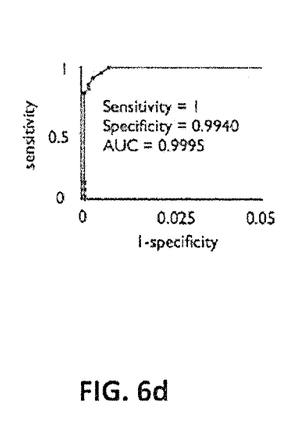
FIG. 6d is a receiver operating characteristic curve depicting the sensitivity and specificity of the measurement capability of a microfluidic device according to aspects of the present invention.

The tradeoff between sensitivity and specificity was characterized by generating an ROC curve that summarizes the results described above. For droplets with an approximate SNR~1, FIG. 6d depicts an area under the curve, AUC=0.9995, demonstrating the ability to robustly monitor parallel streams of droplets using only a single photodetector.

Characterizing the Effect of Design Parameter Choices on Performance

To characterize and to aid in the design of the system, a model was used to simulate a range of parameters. The model was carried out using MATLAB. Briefly, a point in time $t_p$ that a droplet passes through a channel, and the specific channel the droplet passes through n are generated stochastically using random number generators. The signal from the passing droplet is created using the mask pattern $V_d(t)=m(n,x/v-t_p)+V_d(t)$, scaled by the droplet velocity v and placed into the output signal $V_d(t)$ at time point tp. N droplets are iteratively placed. Gaussian noise is added to the signal to the appropriate signal to noise ratio SNR. The model was verified by direct comparison to experimental data. Using this model, the limits of the detection strategy were determined, which sets the groundwork for future applications and development.

Figure 7A:
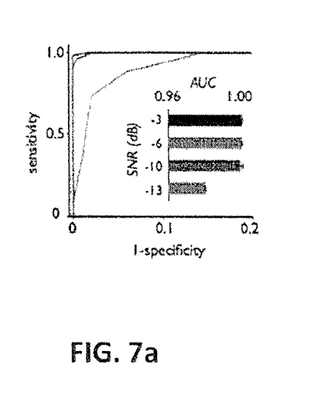
FIG. 7a is a receiver operating characteristic curve depicting the effect of the signal to noise ratio on the sensitivity and specificity of a microfluidic device according to aspects of the present invention.

It was investigated how the sensitivity and specificity of droplet detection were a function of the signal to noise ratio (SNR) of the photodetector. For the setup used in this study (L=100 bits, c=4 channels) it was found, as depicted by FIG. 7a, that droplets could be detected with high sensitivity and accuracy (AUC=0.9991) with an SNR as low as −10 dB (0.1). Below an SNR of −13 dB (0.05) the sensitivity and specificity began to fall off rapidly. The ability to resolve droplets when the signal is only 5% of noise, enables weakly fluorescent droplets to be resolved using a simple, lens free photodetector.

Figure 7B:
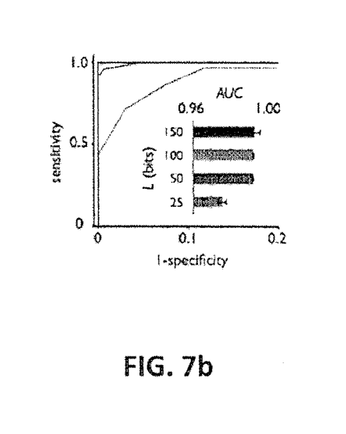
FIG. 7b is a receiver operating characteristic curve depicting the effect of the number of bits of the mask pattern on the sensitivity and specificity of a microfluidic device according to aspects of the present invention.

Next, the effect of the number of bits in the mask L on performance was measured. For a system matched to the prototype (SNR=−6 dB, c=4 channels) it was found that the mask could be reduced to a length to as low as L=100 bits (AUC=0.999), without a significant reduction in performance. Below L=50 bits, sensitivity and specificity fell off rapidly. The increase in performance with bit length may be attributed to two factors: 1) as the number of bits is increased, the droplet is effectively measured more instances, leading to an increase in the effective SNR by signal averaging ~$\sqrt{L}$; and 2) as the number of bits is increased, the cross-correlation between the channels ma*mb≠a correspondingly decreases, which reduces the background signal in $\psi_a$ when a droplets pass through a channel b≠a.

Characterizing the Limitations for Increasing the Number of Channels

Figure 7C:
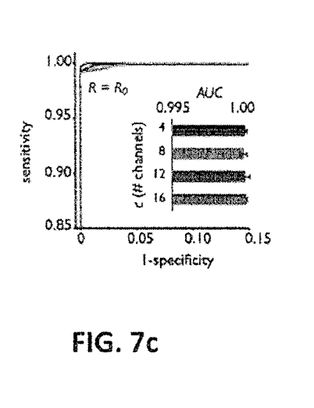
FIG. 7c is a receiver operating characteristic curve depicting the effect of the number of passages on the sensitivity and specificity of a microfluidic device according to aspects of the present invention.

Finally, the model system was used to demonstrate the feasibility of adding more channels than the c=4 demonstrated in the prototype. In our first experiment, the total droplet rate was kept constant R=$R_0$, such that the average number of droplets in the detection region was ~1. As shown in FIG. 7c, for a device matched to the prototype (L=100 bits, SNR=−6 dB), it was found that as the number of channels increased from c=4 to 16, the sensitivity and specificity remained constant. This result may be attributable to several factors including: 1) the increase in correlation $m_a*m_{b\neq a}$ between channels as c is increased from 4 to 16 is insignificant, and 2) because the number of uncorrelated masks that can be generated from L=100 bits is much larger than c.31 2. As the number of channels is increased, there are more correlation vectors $\psi_a$ per droplet. The peak-finding algorithm identifies peaks by comparing peak height to the local variance in the other vectors $\psi_{b\neq a}$. As the number of channels c is increased, there was increased averaging, which decreases the false positives and negatives.

Figure 7D:
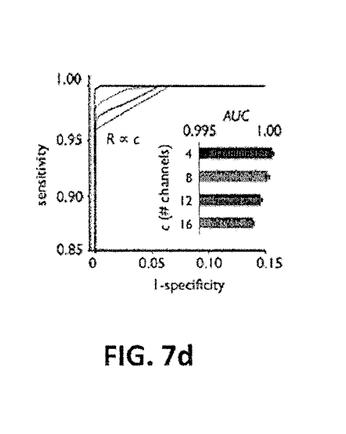
FIG. 7d is a receiver operating characteristic curve depicting the effect the number of passages and the number of droplets on the sensitivity and specificity of a microfluidic device according to aspects of the present invention.
Figure 8:
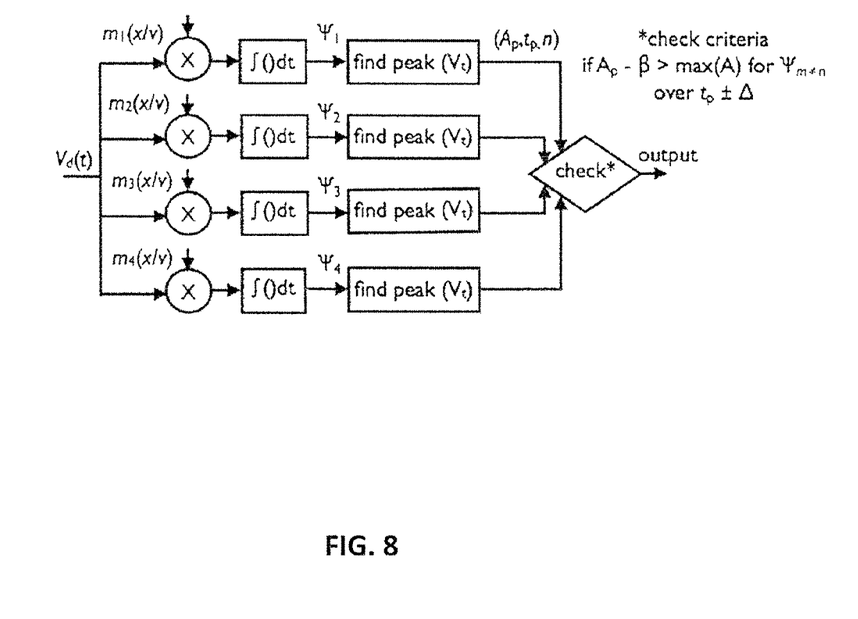
FIG. 8 is a flow diagram schematic of signal measurement according to aspects of the present invention.

As shown by FIG. 7d, the chip's ability to multiplex may be somewhat limited by the droplet density, with performance falling off when the average number of droplets in the detection region increased beyond ~2. Because the position of the droplets in the channel followed Poisson statistics, as the average number of droplets in the detection region became greater than 2, it became increasingly likely that >5 droplets may be found in the detection region at any given instance, at which point the detector's ability to resolve individual events was affected. To test this phenomenon, rather than keep the total droplet rate constant R=R0, the droplet rate per channel was kept constant R∝c. The droplet rate was selected such that for 4 channels, there was on average one droplet in the detection region at a time, and the rate increased proportionally as channels were added. The performance of the device fell off proportionally with each added channel.

Utilizing Multiple Fluorescent Dyes and Multiple Light Wavelengths

Figure 9A:
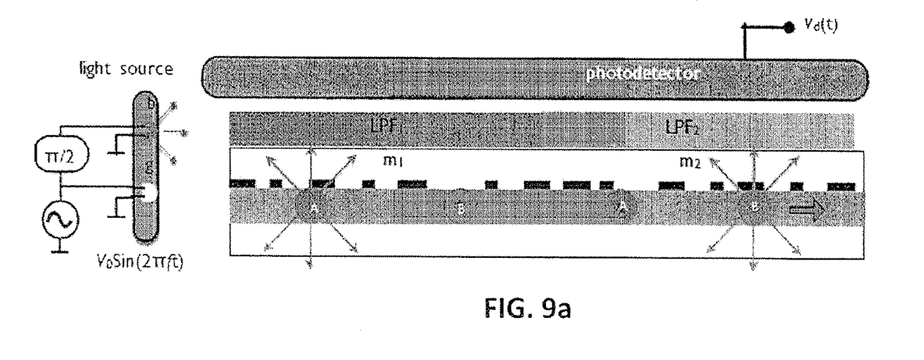
FIG. 9a is a cross-sectional schematic illustration of a microfluidic device providing light at two different wavelengths according to aspects of the present invention.

By modulating both the excitation wavelength and the emission wavelengths of a fluorescent signal to detect multiple fluorescent dyes within each droplet, detection of the analytes in the droplets may be improved. In FIG. 9a the two fluorescent dyes, fluorescein and rhodamine B, respectively have excitation wavelengths corresponding to a light wavelength of 530 nm, associated with the color green, and a light wavelength of 460 nm, associated with the color blue. Desirably, the two light wavelengths used to excite the fluorescent dyes are modulated out of phase from one another.

Figure 9B:
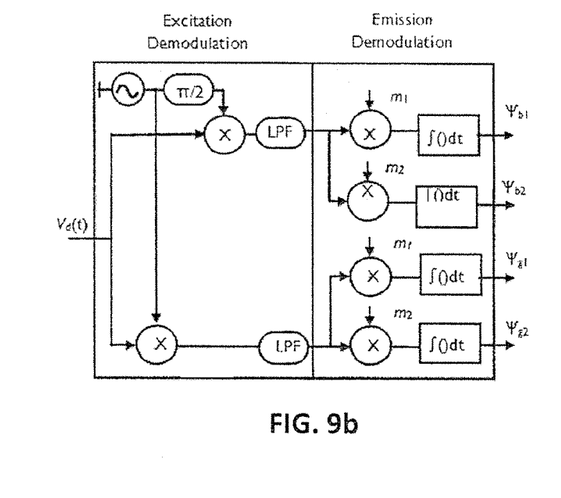
FIG. 9b is a flow diagram schematic of a two-step demodulation for the excitation and the emission spectra according to aspects of the present invention.
Figure 9C:
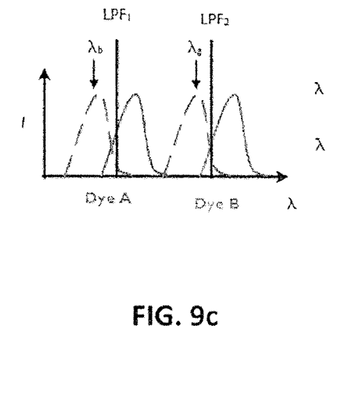
FIG. 9c is an illustration of the excitation and emission spectra of two dyes configured to provide two different signals according to aspects of the present invention.

An example of the excitation spectra, shown as a dashed line, and the emission spectra, shown as a solid line, resulting from the fluorescein and rhodamine B dyes are illustrated in FIG. 9c.

Two different long-pass optical filters are employed to resolve the emission spectra produced by the droplets. The two filters will be spatially separated such that each droplet passes under the filters sequentially. In this example, each of the two filters are configured to correspond to a single wavelength, e.g., the green light wavelength or the blue light wavelength, such that one filter blocks the excitation resulting from the blue light wavelength and the other filter blocks the excitation resulting from the green light wavelength. The two mask patters may be co-located with the filters to demodulate the response from reach filter.

Figure 9D:
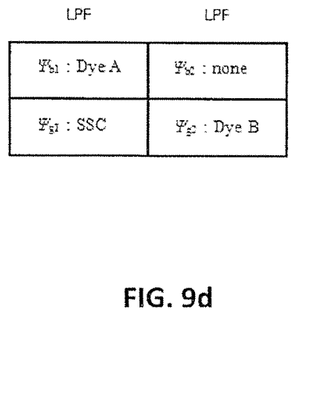
FIG. 9d is a schematic illustration for the results of the two-step demodulation of FIG. 9b.

The signals from the photodetector are demodulated to independently measure the two signals received from the two dyes. FIG. 9b illustrates a two-step demodulation method, whereby the demodulation of the excitation and the emission occur sequentially. In this example, demodulation results in four possible combinations associated with the response from the two excitation sources and two emission filters, as illustrated in FIG. 9d.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A microfluidic device for analyzing droplets comprising
   a substrate;
   a microfluidic channel formed on the substrate, the microfluidic channel including a plurality of passages, each of the plurality of passages having a mask pattern configured to modulate a signal of a respective droplet passing through that passage, such that droplets passing through the plurality of passages produce a plurality of signals; and
   a detector configured to detect the plurality of signals,
   wherein the mask pattern of each of the plurality of passages comprises one or more signal emitting portions and one or more signal dampening portions, which correspond to a binary pattern of at least 100 bits.

2. The microfluidic device of claim 1, wherein the mask pattern is different for each of the plurality of passages.

3. The microfluidic device of claim 2, wherein the one or more signal emitting portions are transparent portions and the one or more signal dampening portions are opaque portions.

4. The microfluidic device of claim 3, wherein the transparent portions and the opaque portions correspond to a binary pattern of 100 to 125 bits.

5. The microfluidic device of claim 1, wherein the mask pattern comprises one or more signal emitting portions configured to permit at least a portion of the signal to be detected by the detector.

6. The microfluidic device of claim 5, wherein the one or more signal emitting portions include at least two states of transparency.

7. The microfluidic device of claim 1, wherein the signal is selected from the group consisting of fluorescence, magnetic, dielectric, and ultrasound.

8. The microfluidic device of claim 3, wherein the signal is a fluorescence signal and the detector is a photodetector.

9. The microfluidic device of claim 8, further comprising an illuminator configured to illuminate the plurality of passages.

10. The microfluidic device of claim 9, wherein the illuminator is configured to alternate between illuminating and not illuminating the plurality of passages.

11. The microfluidic device of claim 9, wherein the illuminator is configured to illuminate the plurality of passages using two or more light wavelengths.

12. The microfluidic device of claim 11, wherein the illuminator is configured to modulate the two or more light wavelengths out of phase with one another.

13. The microfluidic device of claim 11, further comprising an optical filter positioned between the mask pattern and the photodetector.

14. The microfluidic device of claim 13, wherein at least one additional optical filter is positioned between the mask pattern and the photodetector, the optical filter and the at least one additional optical filter each corresponding to a single wavelength of the two or more light wavelengths.

15. The microfluidic device of claim 1, wherein the droplet contains one or more analytes from the group consisting of emulsifications, beads, cells, pathogens, DNA, RNA, nucleic acids, pollutants, and combinations thereof.

16. A microfluidic device for analyzing droplets comprising
- a substrate;
- a microfluidic channel formed on the substrate, the microfluidic channel including a plurality of passages, each of the plurality of passages having a mask pattern, the mask pattern configured to modulate a fluorescence signal of a droplet passing through the passage, such that droplets passing through the plurality of passages produce a plurality of fluorescence signals; and
- a detector configured to detect the plurality of fluorescence signals,
- wherein the mask pattern of each of the plurality of passages comprises one or more signal emitting portions and one or more signal dampening portions, which correspond to a binary pattern of at least 100 bits.

17. The microfluidic device of claim 16, wherein the detector is a photodetector.

18. The microfluidic device of claim 17, wherein the mask pattern is different for each of the plurality of passages.

19. The microfluidic device of claim 18, further comprising a circuit configured to correlate each of the plurality of fluorescence signals with a mask pattern.

20. The microfluidic device of claim 16, wherein the droplet produces two or more fluorescence signals, each fluorescence signal corresponding to a different light wavelength.

21. The microfluidic device of claim 20, further comprising two or more filters configured to demodulate the two or more fluorescence signals.

22. A method of analyzing a plurality of droplets with a microfluidic device having a microfluidic channel formed on a substrate, the microfluidic channel including a plurality of passages, the method comprising
- passing a plurality of droplets through the plurality of passages,
- wherein each of the plurality of passages has a mask pattern;
- modulating a plurality of signals from the plurality of droplets using the mask pattern; and
- detecting the plurality of signals,
- wherein the mask pattern of each of the plurality of passages comprises one or more signal emitting portions and one or more signal dampening portions, which correspond to a binary pattern of at least 100 bits.

23. The method of claim 22, wherein the mask pattern is different for each of the plurality of passages.

24. The method of claim 23, further comprising the step of correlating each of the plurality of signals to the corresponding mask pattern.

25. The method of claim 22, wherein each of the plurality of masks patterns comprises one or more signal emitting portions and one or more signal dampening portions.

26. The method of claim 25, wherein the one or more signal emitting portions are transparent portions and the one or more signal dampening portions are opaque portions.

27. The method of claim 26, wherein the transparent portions and the opaque portions correspond to a binary pattern of 100 to 125 bits.

28. The method of claim 25, wherein the one or more signal emitting portions form a pattern of various states of transparency.

29. The method of claim 22, wherein the plurality of signals is one or more of fluorescence, magnetic, dielectric, and ultrasound.

* * * * *

UNITED STATES PATENT AND TRADEMARK OFFICE
CERTIFICATE OF CORRECTION

PATENT NO. : 10,473,590 B2  
APPLICATION NO. : 15/503592  
DATED : November 12, 2019  
INVENTOR(S) : Issadore et al.

Page 1 of 1

It is certified that error appears in the above-identified patent and that said Letters Patent is hereby corrected as shown below:

On the Title Page

Item [57], Under heading ABSTRACT, Page no. 2, Line no. 2, Replace "using mask patterns, formed on the passages; and detecting" with --using mask patterns formed on the passages; and detecting--

In the Claims

Under Column no. 16, Claim no. 25, Line no. 22, Replace "of masks patterns comprises one or more signal emitting" with --of mask patterns comprises one or more signal emitting--

Signed and Sealed this
Twenty-fifth Day of February, 2020

Andrei Iancu
*Director of the United States Patent and Trademark Office*